(12) United States Patent
Anand et al.

(10) Patent No.: US 12,397,007 B2
(45) Date of Patent: *Aug. 26, 2025

(54) METHODS OF TREATMENT WITH COMBINATIONS OF CANNABIDIOL AND PSILOCYBIN

(71) Applicant: ECP Pharma, Richmond Hill (CA)

(72) Inventors: Nitin Anand, Richmond Hill (CA); Michael E. Hoffer, Miami, FL (US); Moiz Rangwalla, Richmond Hill (CA); Andy Mera, Richmond Hill (CA); Gilberto Iragorri, Richmond Hill (CA)

(73) Assignee: ECP Pharma, Richmond Hill (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/416,953

(22) Filed: Jan. 19, 2024

(65) Prior Publication Data

US 2024/0156843 A1    May 16, 2024

Related U.S. Application Data

(63) Continuation of application No. 18/045,843, filed on Oct. 12, 2022, now Pat. No. 11,911,402.

(60) Provisional application No. 63/255,191, filed on Oct. 13, 2021.

(51) Int. Cl.
*A61K 31/675* (2006.01)
*A61K 31/05* (2006.01)
*A61K 31/28* (2006.01)
*A61P 25/28* (2006.01)

(52) U.S. Cl.
CPC ............ *A61K 31/675* (2013.01); *A61K 31/05* (2013.01); *A61P 25/28* (2018.01)

(58) Field of Classification Search
CPC ...... A61K 31/675; A61K 31/358; A61P 25/28
See application file for complete search history.

(56) References Cited

U.S. PATENT DOCUMENTS

| 2018/0221396 | A1  | 8/2018  | Chadeayne |
| 2018/0318529 | A1† | 11/2018 | Davidson  |
| 2019/0105313 | A1  | 4/2019  | Stamets   |
| 2019/0142851 | A1† | 5/2019  | Chadeayne |

FOREIGN PATENT DOCUMENTS

| WO | 2021/072530 A1 |   | 4/2021 |
| WO | 2021072530     | † | 4/2021 |
| WO | 2022/115796 A1 |   | 6/2022 |

† cited by third party

*Primary Examiner* — Sikarl A Witherspoon
(74) *Attorney, Agent, or Firm* — Chiesa Shahinian & Giantomasi PC

(57) ABSTRACT

The disclosure relates to methods for treating brain injuries that include administering to a patient a first dosage of about 100 mg to about 500 mg of cannabidiol (CBD) and administering to the patient, concomitantly with the first dosage, a second dosage of about 1 to about 10 milligrams of Psilocybin.

19 Claims, 11 Drawing Sheets
(11 of 11 Drawing Sheet(s) Filed in Color)

METHODS OF TREATMENT WITH COMBINATIONS OF CANNABIDIOL AND PSILOCYBIN

This application is a Continuation of prior-filed U.S. patent application Ser. No. 18/045,843, filed Oct. 12, 2022, which claims the benefit under 35 U.S.C. 119 of U.S. Provisional Patent Application No. 63/255,191, filed Oct. 13, 2021; the disclosures of all of which are incorporated herein by reference in their entirety.

BACKGROUND

Traumatic Brain Injury ("TBI") is a brain injury resulting from an impact to the head, damaging the brain. TBI is a major cause of disability and death, with 3 million emergency room visits and over 230,000 hospitalizations due to TBI each year in the United States alone. There are also 5.3 Million Americans living with the effects of TBI (a 53% increase from ten years ago).

Health problems caused by TBI can be short-term or life-long. TBI can affect a person both physically as well as cognitively/mentally.

TBI severity is typically separated into categories of mild, moderate, and severe. Mild TBIs ("mTBI") are commonly referred to as concussions and can be accompanied by physical symptoms such as headache, nausea, vomiting, fatigue, speech problems and dizziness or loss of balance, as well as cognitive/behavioral symptoms including loss of consciousness, changes to sleep patterns, and memory, concentration, and/or mood problems.

Moderate to severe TBI results in physical damage to the brain including bruising, torn tissues, and bleeding, which is accompanied by physical symptoms including loss of consciousness, seizures, persistent headache, loss of coordination, vomiting and nausea, pupil dilation, and inability to awaken from sleep. Cognitive symptoms from moderate to severe TBI include confusion, agitation, slurred speech and consciousness disorders including coma. TBI in children can also result in developmental issues and impact the child's behavior and cognitive skills. Car crashes, assaults, falls, and firearm related incidents are leading causes of TBI.

Vestibular and/or oculomotor tests can detect the presence of mTBI with a high degree of sensitivity (about 85%) and the absence of mTBI with a high degree of specificity (about 90%). An example of such a test is rotational chair testing which uses infra-red light to record eye movements, which are then analyzed and provide information about the patient's brain condition. Patients are seated in a dark chamber and equipped with head-mounted goggles with two high speed built-in infra-red tracking sensors. The patient is then rotated and/or maneuvered through a series of positions, while eye motions in response to a target is recorded. Optokinetic stimuli consisting of a full field of horizontally moving illuminated points created by a rotating projector or with a galvanometer/servo-controlled 650 nm laser are projected onto the testing surface, and the visual and auditory reaction time eye data and feedback from motion are acquired at 100 Hz and then analyzed using software. Portable versions of these tests can be developed to provide diagnostic capabilities at the point of injury. One such portable device, the I-Portal Portable Assessment System ("I-PAS") Goggles, is currently FDA approved for the diagnosis of mTBI.

There are currently no approved therapies for the treatment of mTBI. In the field, practitioners do not have a well-established treatment regimen and in most cases only offer symptomatic relief of headaches using non-steroidal anti-inflammatory medications.

PTSD is an anxiety disorder that results from a patient who witnesses or is exposed to a traumatic event that is threatening. The patient re-experiences the event, such as through intrusive memories, nightmares, a sense of reliving the trauma, and becomes psychologically or physiologically distressed when reminded of the trauma. The patient will often display avoidance symptoms, which can include active avoidance of thoughts, feelings, or reminders of the trauma, inability to recall some aspect of the trauma, withdrawal from others, or emotional numbing and will suffer from insomnia, irritability, difficulty concentrating, hypervigilence, or heightened startle response. These symptoms are known to cause marked impairment to a patient's functioning at least 1 month after the trauma. If the traumatic reactions occur in the initial month following a trauma, the disorder is known as acute stress disorder (ASD).

Approximately eight (8) million new cases a year of PTSD are recorded, with about 6.8% of the U.S. population suffering from PTSD at some point in their lifetime and a rate of about 2.1%-7.8% of the world's population affected by the disorder.

PTSD and ASD can seriously hinder the patient's ability to participate in normal daily tasks and interfere with social and/or work situations.

Post-traumatic stress disorder (PTSD) and traumatic brain injury (TBI) often coexist because brain injuries are often sustained in traumatic experiences. Longitudinal studies examining the combined impact of PTSD and TBI indicate enduring psychological and cognitive effects that remain intertwined long after exposure to trauma, including poor physical health, reduced quality of life, and negative psychological well-being. The physical and cognitive effects of the combined disorders are dramatically greater than for either disorder alone. Over about 50% of mild TBI cases are concurrent with ASD and/or PTSD.

Cannabidiol (CBD) is a 21-carbon terpenophenolic compound which is formed following decarboxylation from a naturally occurring cannabidiolic acid precursor found in *cannabis* plants, or produced synthetically in a lab.

CBD acts as a $CB_2$ agonist and presents a broad range of anti-inflammatory and immune inhibitory effects. There is extensive research into the cannabinoid $CB_2$ receptor as a target for inflammation-dependent neurodegeneration. CBD has been tested in Phase 3 clinical trials as a treatment for various disorders.

CBD has been studied for use in patients with epilepsy, as well as for anxiety and pain disorders, Parkinson disease, Multiple sclerosis, Crohn's disease, PTSD, sleep disorders, and other chronic conditions, and cannabidiol is the active ingredient in an approved drug indicated for the treatment of seizures associated with Lennox-Gastaut syndrome, Dravet syndrome, or tuberous sclerosis complex (TSC).

Psilocybin (4-phosphoryloxy-N,N-dimethyltryptamine) is a psychedelic prodrug that is cleaved by alkaline phosphatases in the body to generate the biologically active compound, psilocin. Psilocybin is produced in nature by various species of fungi but can also be produced synthetically in a lab. Psilocybin and its active dephosphorylated metabolite psilocin belong to the group of tryptamine/indolamine hallucinogens and are structurally related to serotonin. As a result, psilocin can bind to serotonergic receptors in the brain and exhibit psychedelic effects. Psilocin is a powerful agonist of many various serotonin (5HT) receptors in the central nervous system (CNS), but it binds with high affinity to 5HT2A, which is thought to be the receptor most responsible for its psychoactive effects. Psilocybin is often used recreationally as a result of its psychedelic effects. Also present in small amounts in Psilocybin compounds are baeocystin and norbaeocystin.

Research has shown that psilocybin reliably induces profound changes in sensory perception, emotion, thought, and sense of self, characterized by marked alterations in all mental functions, including perception, mood, volition, cognition, and self-experience. These changes are often referred to as mystical-type experiences. Measures of mystical-type experience occurring during psilocybin treatment have been repeatedly observed to predict later effects on behavior and emotions, including reductions in depressive and anxious symptoms.

Psilocybin has been studied clinically for the treatment of anxiety and depression associated with terminal cancer, treatment resistant depression, obsessive-compulsive disorder, and smoking cessation, with a good safety profile and included short-term adverse effects include fatigue, headaches, and lack of energy.

Animal studies have also been conducted to study the behavior effects of psilocybin. Studies in rodents showed that psilocybin can create long-term behavioral outcomes comparable to those of traditional antidepressant treatments in measures of coping strategy and cognitive function.

TBI and stroke are known to alter hippocampal neurogenesis in murine models, and acute administration of psilocybin to mice alters hippocampal neurogenesis in a non-linear fashion. Low doses may lead to increased neurogenesis while higher doses appear to inhibit neurogenesis. Increased neurogenesis has also been seen when high dose psilocybin was administered once per week, avoiding the issue of rapid tolerance buildup via 5HTR downregulation.

There are currently no effective pharmaceutical treatments for TBI, PTSD, ASD, or other anxiety disorders and chronic conditions with symptoms of pain, anxiety, or insomnia.

SUMMARY

In accordance with one or more embodiments, methods of treatment and inhibition are provided.

There remains a need for additional and improved methods of diagnosing and treating TBI, PTSD, ASD, and other anxiety disorders and chronic conditions with symptoms of pain, anxiety, or insomnia. The present disclosure is a method of treating one or more diseases, by concomitantly administering pharmaceutical compositions of CBD, Psilocybin, or similar compounds, either in a single drug product or as two separate drug products. These diseases include mTBI, TBI, PTSD, ASD, and other anxiety disorders and chronic conditions with symptoms of pain, anxiety, or insomnia.

The present disclosure also finds the surprising and unexpected synergy from the combination of the CBD and Psilocybin as an effective treatment for mTBI, TBI, PTSD, ASD, and other anxiety disorders and chronic conditions with symptoms of pain, anxiety, or insomnia.

The present disclosure includes a method for using 1-PAS goggles to detect eye movements in response to stimuli which, when analyzed, can detect the presence of mTBI with a high degree of sensitivity.

The present disclosure also includes a method for cognitive tests, Vestibular/Ocular Motor Tests including Vestibular/Ocular Motor Screening (VOMS), Visual Vertigo Analog Scale (VVAS) Dynamic Visual Acuity Test (DVAT) to detect and assess symptoms, including to measure effectiveness of the method of treatment disclosed herein.

The present disclosure also includes measuring symptoms using the Modified Balance Error Scoring System (mBESS), Dizziness Handicap Inventory (DHI), Neurobehavioral Symptom Inventory (NSI), Behavioral Symptom Inventory-18 (BSI-18), and Pittsburgh Sleep Quality Index (PSQI).

In a preferred embodiment, the method of treating patients with TBI, PTSD, ASD, or other anxiety disorders and chronic conditions with symptoms of pain, anxiety, or insomnia results in improved performance compared to placebo medicine with respect to measures of balance function, cognitive function, and stress disorders.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of this specification, illustrate embodiments of the disclosure, and, together with the summary given above, and the detailed description of the embodiments below, serve as a further explanation and disclosure to explain and/or illustrate embodiments of the disclosure.

DETAILED DESCRIPTION

Figure 1:
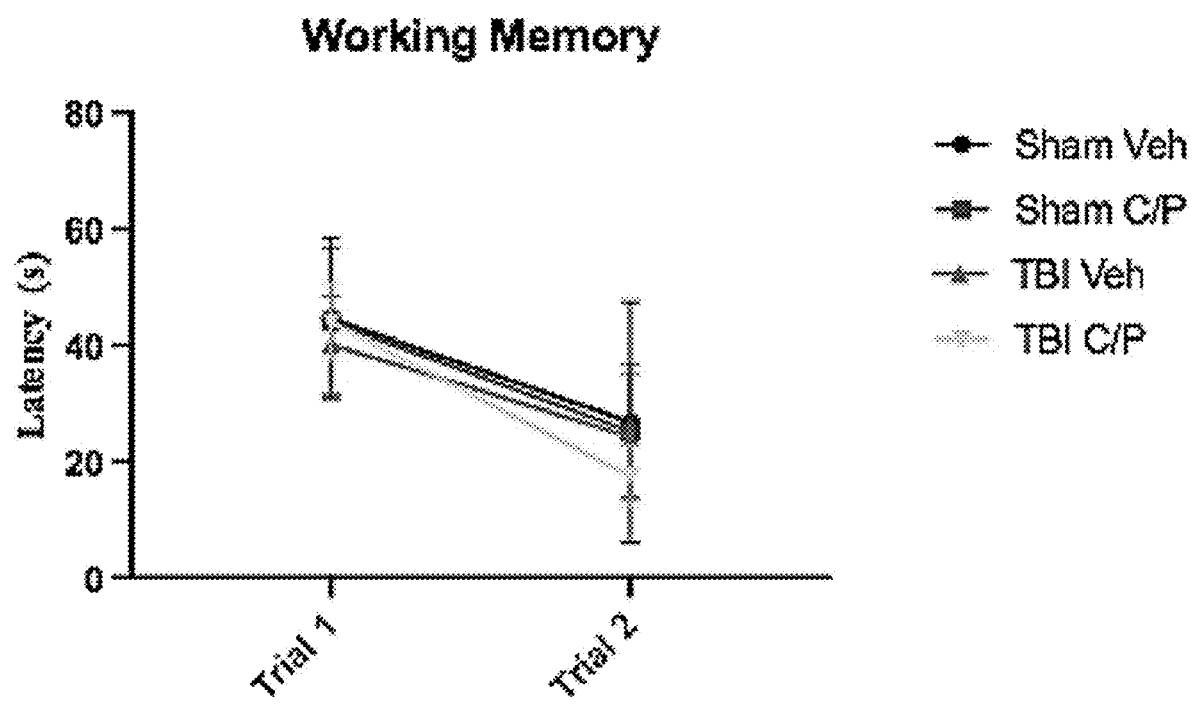
FIG. 1 is a graphical illustration of results of a Rat Fluid Percussion Model.

It is noted that the drawings of the present application are provided for illustrative purposes only and, as such, the drawings are not drawn to scale. It is also noted that like and corresponding elements are referred to by like reference numerals.

In the following description, numerous specific details are set forth, such as particular structures, components, materials, dimensions, processing steps and techniques, in order to provide an understanding of the various embodiments of the present application. However, it will be appreciated by one of ordinary skill in the art that various embodiments of the present application may be practiced without these specific details. In other instances, well-known structures or processing steps have not been described in detail in order to avoid obscuring the present application.

As used herein, the term "substantially" or "substantial", is equally applicable when used in a negative connotation to refer to the complete or near complete lack of an action, characteristic, property, state, structure, item, or result. For example, a surface that is "substantially" flat would either be completely at, or so nearly flat that the effect would be the same as if it were completely flat.

As used herein, terms defined in the singular are intended to include those terms defined in the plural and vice versa.

As used in this specification and its appended claims, terms such as "a", "an" and "the" are not intended to refer to only a singular entity, but include the general class of which a specific example may be used for illustration, unless the context dictates otherwise. The terminology herein is used to describe specific embodiments of the invention, but their usage does not delimit the invention, except as outlined in the claims.

Unless otherwise indicated, all numbers expressing quantities of ingredients, properties such as molecular weights, reaction conditions, and so forth as used in the specification and claims are to be understood as being modified in all instances by the term "about." Accordingly, unless indicated to the contrary, the numerical parameters in the specification and claims are approximations that may vary depending upon the desired properties sought to be obtained by the present invention. At the very least, and without limiting the application of the doctrine of equivalents to the scope of the claims, each numerical parameter should at least be construed in light of the number of reported significant digits and by applying ordinary rounding techniques. Notwithstanding that the numerical ranges and parameters describing the broad scope of the invention are approximations, the numerical values in the specific examples are reported as precisely as possible. Any numerical value, however, inherently contains standard deviations that necessarily result from the errors found in the numerical value's testing measurements.

Thus, reference herein to any numerical range expressly includes each numerical value (including fractional numbers and whole numbers) encompassed by that range. To illustrate, reference herein to a range of "at least 50" or "at least about 50" includes whole numbers of 50, 51, 52, 53, 54, 55, 56, 57, 58, 59, 60, etc., and fractional numbers 50.1, 50.2 50.3, 50.4, 50.5, 50.6, 50.7, 50.8, 50.9, etc. In a further illustration, reference herein to a range of "less than 50" or "less than about 50" includes whole numbers 49, 48, 47, 46, 45, 44, 43, 42, 41, 40, etc., and fractional numbers 49.9, 49.8, 49.7, 49.6, 49.5, 49.4, 49.3, 49.2, 49.1, 49.0, etc. In yet another illustration, reference herein to a range of from "5 to 10" includes whole numbers of 5, 6, 7, 8, 9, and 10, and fractional numbers 5.1, 5.2, 5.3, 5.4, 5.5, 5.6, 5.7, 5.8, 5.9, etc.

In the discussion and claims herein, the term "about" indicates that the value listed may be somewhat altered, as long as the alteration does not result in nonconformance of the process or structure to the illustrated embodiment. For example, for some elements the term "about" can refer to a variation of ±0.1%, for other elements, the term "about" can refer to a variation of ±1% or ±10%, or any point therein.

Reference now will be made in detail to embodiments of the disclosure. It will be apparent to those skilled in the art that various modifications and variations can be made in the present disclosure without departing from the scope or spirit of the disclosure. For instance, features illustrated or described as part of one embodiment can be used on another embodiment to yield a still further embodiment.

One embodiment of the present disclosure is a method for treating brain injuries that includes administering to a patient a first dosage of about 100 mg to about 500 mg of cannabidiol (CBD).

The patient can be any mammal. As used herein, the term "mammal" refers to any mammalian species such as a human, mouse, rat, dog, cat, hamster, guinea pig, rabbit, livestock, and the like.

As used herein, the term "administer," "administering" or "administration" refers to the act of administering or having a compound or pharmaceutical composition administered to the body of a subject by any suitable method noted in this disclosure or otherwise known in the art. Administration of a compound or a pharmaceutical composition includes the prescription of a compound or a pharmaceutical composition to be administered in the body of a patient. Exemplary administration forms include oral dosage forms, such as tablets, capsules, syrups, suspensions; injectable dosage forms, such as intravenous (IV), intramuscular (IM) or intraperitoneal (IP) dosage forms; transdermal, which include creams, jellies, powders or patches; oral dosage forms; inhalation powders, aerosols, suspensions and rectal suppositories. The administration of the first dosage and the second dosage discussed herein can be in separate dosage forms (which may be the same as each other or different), or in a single dosage form. Additionally, either of the first dosage and the second dosage can be one of an immediate, or nearly immediate, release delivery system or a sustained release delivery system. The dosages of the disclosure can be prepared with pharmaceutically acceptable excipients, diluents or carriers. According to the desired properties of the pharmaceutical composition, any number of ingredients may be selected, alone or in combination, based upon their known uses in formulating pharmaceutical compositions. Suitable carriers, diluents and excipients are well-known to those skilled in the art and include pharmaceutically acceptable excipients such as carbohydrates, waxes, water soluble and/or swellable polymers, hydrophilic or hydrophobic materials, gelatin, oils, solvents, water, and the like. The formulations may also include one or more buffers, stabilizing agents, diluents, surfactants, wetting agents, lubricating agents, glidants, emulsifiers, disintegrants, suspending agents, preservatives, antioxidants, opaquing agents, glidants, antioxidants, compression and processing aids, colorants, sweeteners, perfuming agents, flavoring agents and other known additives.

As used herein, the term CBD refers to any natural or synthetic cannabinoid, and solvates, hydrates and pharmaceutically acceptable salts thereof, including but not limited to Cannabigerolic Acid (CBGA), Cannabigerolic Acid monomethylether (CBGAM), Cannabigerol (CBG), Cannabigerol monomethylether (CBGM), Cannabigerovarinic Acid (CBGVA), Cannabigerovarin (CBGV), Cannabichromenic Acid (CBCA), Cannabichromene (CBC), Cannabichromevarinic Acid (CBCVA), Cannabichromevarin (CBCV), Cannabidiolic Acid (CBDA), Cannabidiol (CBD), Cannabidiol monomethylether (CBDM), Cannabidiol-$C_4$ (CBD-$C_4$), Cannabidivarinic Acid (CBDVA), Cannabidivarin (CBDV), Cannabidiorcol (CBD-$C_1$), Tetrahydrocannabinolic acid A (THCA-A), Tetrahydrocannabinolic acid B (THCA-B), Tetrahydrocannabinolic Acid (THCA), Tetrahydrocannabinol (THC), Tetrahydrocannabinolic acid $C_4$(THCA-$C_4$), Tetrahydrocannabinol $C_4$(THC-$C_4$), Tetrahydrocannabivarinic acid (THCVA), Tetrahydrocannabivarin (THCV), Tetrahydrocannabiorcolic acid (THCA-$C_1$), Tetrahydrocannabiorcol (THC-$C_1$), $\Delta^7$-cis-iso-tetrahydrocannabivarin, $\Delta^8$-tetrahydrocannabinolic acid ($\Delta$8-THCA), Cannabivarinodiolic (CBNDVA), Cannabivarinodiol (CBNDV), $\Delta^8$-tetrahydrocannabinal ($\Delta^8$-THC), $\Delta^9$-tetrahydrocannabinol ($\Delta^9$-THC), Cannabicyclolic acid (CBLA), Cannabicyclol (CBL), Cannabicyclovarin (CBLV), Cannabielsoic acid A (CBEA-A), Cannabielsoic acid B (CBEA-B), Cannabielsoin (CBE), Cannabivarinselsoin (CBEV), Cannabivarinselsoinic Acid (CBEVA), Cannabielsoic Acid (CBEA), Cannabielvarinsoin (CBLV), Cannabielvarinsoinic Acid (CBLVA), Cannabinolic acid (CBNA), Cannabinol (CBN), Cannabivarinic Acid (CBNVA), Cannabinol methylether (CBNM), Cannabinol-$C_4$(CBN-$C_4$), Cannabivarin (CBV), Cannabino-$C_2$(CBN-$C_2$), Cannabiorcol (CBN-$C_1$), Cannabinodiol (CBND), Cannabinodiolic Acid (CBNDA), Cannabinodivarin (CBDV), Cannabitriol (CBT), 10-Ethoxy-9-hydroxy-As-tetrahydrocannabinol, 8,9-Dihydroxy-$\Delta^{8a(10a)}$-tetrahydrocannabinol (8,9-Di-OH-CBT-$C_5$), Cannabitriolvarin (CBTV), Ethoxy-cannabitriolvarin (CBTVE), Dehydrocannabifuran (DCBF), Cannbifuran (CBF), Cannabichromanon (CBCN), Cannabicitran (CBT), 10-Oxo-$\Delta^{8a(10a)}$-tetrahydrocannabinol (OTHC), $\Delta^9$-cis-tetrahydrocannabinol (cis-THC), Cannabiripsol (CBR), 3,4,5,6-tetrahydro-7-hydroxy-alpha-alpha-2-trimethyl-9-n-propyl-2,6-methano-2H-1-benzoxocin-5-methanol (OH-iso-HHCV), Trihydroxy-delta-9-tetrahydrocannabinol (triOH-THC), Yangonin, Epigallocatechin gallate, Dodeca-2E,4E,8Z,10Z-tetraenoic acid isobutylamide, and Dodeca-2E,4E-dienoic acid isobutylamide. CBD can also include compositions that are similar in properties or effects to CBD (including but not limited to lenabasum), derivatives of CBD, modified forms of CBD, or cannabinoids from plants other than *cannabis*. In some embodiments, the CBD can be compounded with pharmaceutically acceptable oils, such as but not limited to sesame seed oil and/or medium chain triglyceride oils which may improve the solubility of the CBD. In other embodiments, the CBD can be compounded with sugar alcohols which can act as a bulking filler material. In other embodiments, the CBD can be compounded with one or more of mannitol, sorbitol, sucrose, starch, gelatin, cellulose, including microcrystalline cellulose, glidants or lubricants to improve flowability and/or fine silica or magnesium stearate. In other embodiments the CBD can be compounded with colorants, which can aid in identification.

In the present disclosure, a brain injury refers to any destruction or degeneration of brain cells is in the brain of a living mammal. Brain injuries can result from direct impacts to the head. Such injuries are for example traumatic brain injury and spinal cord injury. The present disclosure may also be used in treating other neuronal disorders, which include disease, disorder, or condition directly or indirectly affecting the normal functioning or anatomy of a subject's nervous system. The disorder may be a neuronal injury, which can be acute or chronic. Examples of acute injury are those that results from surgery, trauma, compression, contusion, transection or other physical injury, vascular pharmacologic or other insults including hemorrhagic or ischemic damage. Chronic neuronal injury may result from repetitive stress, inflammation/oxidative stress within a neural tissue caused by disease, neurodegenerative or other neurological diseases. The method and compositions provided herein can be beneficial in all diseases where the CSPG matrix is inhibitory for regeneration or maintenance of axons, such as TBI, SCI, multiple sclerosis (MS disease) and amyotrophic lateral sclerosis (ALS).

Traumatic brain injury, "TBI" and mild traumatic brain injury "mTBI" as used herein includes the condition in which a traumatic blow to the head causes damage to the brain or connecting spinal cord, with or without penetrating the skull. It relates more specifically to the actual mechanical damage that occurs at the type of trauma, such as shearing, tearing and stretching of axons, neurons and blood vessels. Usually, the initial trauma can result in expanding hematoma, subarachnoid hemorrhage, cerebral edema, raised intracranial pressure, and cerebral hypoxia, which can, in turn, lead to severe secondary events due to low cerebral blood flow.

In this disclosure the method can further comprise administration to the patient, concomitantly with the first dosage of CBD, a second dosage of 1 to 10 milligrams of Psilocybin. In some embodiments both the first dosage and the second dosage can occur within about 72 hours of the time of injury.

As used herein, "concomitant" means at the same time, nearly the same, or within a short time, and "concomitantly" refers to actions performed at the same time, nearly the same time, or within a short time. As used herein, the terms "concurrent" and "concomitant" are equivalent and may be used interchangeably. The adverbs "concurrently" and "concomitantly" are equivalent and may be used interchangeably. As used herein, the term "concomitant administration" of two or more drugs means administering two or more drugs in a concomitant administration. Events or actions that are "simultaneous" or that occur or are performed "simultaneously" are events that occur or are performed at the same time.

As used herein, "at the same time" means that two events occur or are performed within about five minutes of each other.

As used herein, "nearly the same time" means that two events occur or are performed within about a short time of each other.

As used herein, a "short time", a "short amount of time", a "short period of time", and the like mean a time that is less than about two hours, or less than about one hour, or less than about 45 minutes, or less than about 30 minutes, or less than about 20 minutes, or less than about 10 minutes, or less than about 7 minutes.

As used herein, the term "psilocybin" refers to any natural or synthetic substance with the IUPAC name [3-(2-dimethylaminoethyl)-1H-indol-4-yl] dihydrogen phosphate; CAS Number 520-52-5; chemical formula $C_{12}H_{17}N_2O_4P$; and molar mass 284, 25:2 g-mol-1, and derivatives, modified forms, purified derivatives and homologs thereof, and solvates, hydrates and pharmaceutically acceptable salts thereof. Psilocybin derivatives can include, but are not limited to: [3-(2-Dimethylaminoethyl)-1H-indol-4-yl] dihydrogen phosphate, 4-hydroxytryptamine, 4-hydroxy-N,N-dimethyltryptamine, [3-(2-methylaminoethyl)-1H-indol-4-yl] dihydrogen phosphate, 4-hydroxy-N-methyltryptamine, [3-(aminoethyl)-1H-indol-4-yl] dihydrogen phosphate, [3-(2-trimethylaminoethyl)-1H-indol-4-yl] dihydrogen phosphate, and 4-hydroxy-N,N,N-trimethyltryptamine. Purified psilocybin derivatives can include, but are not limited to: [3-(2-Dimethylaminoethyl)-1H-indol-4-yl] dihydrogen phosphate, 4-hydroxytryptamine, 4-hydroxy-N,N-dimethyltryptamine, [3-(2-methylaminoethyl)-1H-indol-4-yl] dihydrogen phosphate, 4-hydroxy-N-methyltryptamine, [3-(aminoethyl)-1H-indol-4-yl] dihydrogen phosphate, [3-(2-trimethylaminoethyl)-1H-indol-4-yl] dihydrogen phosphate, and 4-hydroxy-N,N,N-trimethyltryptamine. Psilocybin is a naturally occurring predrug compound produced by more than 200 species of fungus. *P. aznreaceus, P. semilanceata,* and *P. cyaneseens* are members of the genus Psilocybe, but psilocybin has also been isolated from about a dozen other genera. As a prodrug, psilocybin is converted by the body to psilocin. Thus, as used herein, "psilocybin" can also refer to any substance that be at least partially converted to psilocin in the body. Additionally, "psilocybin" can encompass other compounds that are similar in properties or effects to psilocybin, such as but not limited to Lysergic acid diethylamide (LSD) and 3,4-Methylenedioxy methamphetamine (MDMA). In other embodiments, the psilocybin can be compounded with sugar alcohols which can act as a bulking filler material. In other embodiments, the psilocybin can be compounded with one or more of vitamin C, mannitol, sorbitol, sucrose, cellulose, including synthetic cellulose, glidants or lubricants to improve flowability and/or fine silica or purified talc. In other embodiments the psilocybin can be compounded with colorants, which can aid in identification. In other embodiments, the psilocybin can be compounded with gums and/or surfactants to facilitate disintegration of the dosage form in the gastrointestinal (GI) tract.

In other embodiments, the first dosage is about 100 mg to about 500 mg CBD and the second dosage is about 1 mg to about 5 mg Psilocybin. In other embodiments, the first dosage is about 100 mg to about 300 mg CBD and the second dosage is about 1.25 mg to about 2.5 mg Psilocybin. In other embodiments of the disclosure, the first dosage administered can be about 250 mg to about 500 mg CBD and the second dosage administered can be about 1.25 mg to about 2.5 mg Psilocybin. Although weights of the various dosages are noted, the administered drugs can be administered in a ratio. For example, a ratio between the first dosage of CBD and the second dosage of psilocybin can be about 100:1 to about 500:1, or about 100:1 to about 250:1. As another example, a ratio between the first dosage of CBD and the second dosage of psilocybin can be about 145:1 to about 155:1. As other examples, the ratio between the first dosage of CBD and the second dosage of psilocybin can be about 150:1, or about 140:1 to about 160:1, or about 130:1 to about 170:1, or about 120:1 to about 180:1, or about 50:1 to about 250:1.

The administration steps of the present disclosure for treating brain injuries can occur at any suitable interval, and in any suitable order. As one example, administration of the first dosage of CBD and the second dosage of psilocybin occurs twice a day for about seven days. In another example, administration of the first dosage of CBD and the second dosage of psilocybin occurs once a day for about seven days.

As noted above, the disclosure is directed to treating brain injuries, the disclosure is also directed to methods of activating both a $CB_2$ receptor and a 5HT receptor of a patient, according to any administration noted above. For example, administration of a first dosage of about 100 mg to about 500 mg of cannabidiol (CBD); and administration, concomitantly with the first dosage, a second dosage of 1 to 10 milligrams of Psilocybin. In other embodiments, the first dosage is about 100 mg to about 300 mg CBD and the second dosage is about 1 mg to about 5 mg Psilocybin. In other embodiments, the first dosage is about 100 mg to about 300 mg CBD and the second dosage is about 1.25 mg to about 2.5 mg Psilocybin. In other embodiments, the first dosage is about 250 mg to about 300 mg CBD and the second dosage is about 1.25 mg to about 2.5 mg Psilocybin.

Although weights of the various dosages are noted, the administered drugs can be administered in a ratio. For example, a ratio between the first dosage of CBD and the second dosage of psilocybin can be about 100:1 to about 500:1. As another example, a ratio between the first dosage of CBD and the second dosage of psilocybin can be about 100:1 to about 250:1. As another example, a ratio between the first dosage of CBD and the second dosage of psilocybin can be about 145:1 to about 155:1. As other examples, the ratio between the first dosage of CBD and the second dosage of psilocybin can be about 150:1, or about 140:1 to about 160:1, or about 130:1 to about 170:1, or about 120:1 to about 180:1, or about 50:1 to about 250:1.

The administration steps of the present disclosure for activating both a $CB_2$ receptor and a 5HT receptor of a patient can occur at any suitable interval, and in any suitable order. As one example, administration of the first dosage of CBD and the second dosage of psilocybin occurs twice a day for about seven days. In another example, administration of the first dosage of CBD and the second dosage of psilocybin occurs once a day for about seven days.

As noted above, the disclosure is directed to treating brain injuries, the disclosure is also directed to methods of reducing a contusion volume of a mammal, according to any administration noted above. For example, administration of a first dosage of about 100 mg to about 500 mg of cannabidiol (CBD); and administration, concomitantly with the first dosage, a second dosage of about 1 to 10 milligrams of Psilocybin. In other embodiments, the first dosage is about 100 mg to about 300 mg CBD and the second dosage is about 1 mg to about 5 mg Psilocybin. In other embodiments, the first dosage is about 100 mg to about 300 mg CBD and the second dosage is about 1.2 mg to about 2.5 mg Psilocybin. In other embodiments, the first dosage is about 250 mg to about 300 mg CBD and the second dosage is about 1.25 mg to about 2.5 mg Psilocybin. Although weights of the various dosages are noted, the administered drugs can be administered in a ratio. For example, a ratio between the first dosage of CBD and the second dosage of psilocybin can be about 100:1 to about 500:1. As another example, a ratio between the first dosage of CBD and the second dosage of psilocybin can be about 100:1 to about 250:1. As another example, a ratio between the first dosage of CBD and the second dosage of psilocybin can be about 145:1 to about 155:1. As other examples, the ratio between the first dosage of CBD and the second dosage of psilocybin can be about 150:1, or about 140:1 to about 160:1, or about 130:1 to about 170:1, or about 120:1 to about 180:1, or about 50:1 to about 250:1.

As used herein, the term "contusion" refers to bruising of the brain, spinal cord and/or peripheral nerve with extravasation of blood and the secondary mass lesion accompanying that hemorrhage.

The administration steps of the present disclosure for reducing a contusion volume of a mammal can occur at any suitable interval, and in any suitable order. As one example, administration of the first dosage of CBD and the second dosage of psilocybin occurs once or twice a day for about seven-ten days. In another example, administration of the first dosage of CBD and the second dosage of psilocybin occurs once a day for about seven-ten days.

Effectiveness testing of treatment efficacy can be conducted, including I-PAS, cognitive tests, Vestibular/Ocular Motor Tests including Vestibular/Ocular Motor Screening (VOMS), Visual Vertigo Analog Scale (VVAS) Dynamic Visual Acuity Test (DVAT). Symptoms were measured using the Modified Balance Error Scoring System (mBESS), Dizziness Handicap Inventory (DHI), Neurobehavioral Symptom Inventory (NSI), Behavioral Symptom Inventory-18 (BSI-18), and Pittsburgh Sleep Quality Index (PSQI) can be conducted to determine the efficacy of any administered dosage.

One embodiment of the disclosure is a method for diagnosing patients with mTBI, administering one or more dosages of CBD alone or CBD in combination with psilocybin, and assessing the effectiveness of treatment using I-PAS, cognitive tests, Vestibular/Ocular Motor Tests including Vestibular/Ocular Motor Screening (VOMS), Visual Vertigo Analog Scale (VVAS) Dynamic Visual Acuity Test (DVAT).

One embodiment of the disclosure is a method for measuring symptoms of mTBI, administering one or more dosages of CBD alone or CBD in combination with psilocybin, and using the Modified Balance Error Scoring System (mBESS), Dizziness Handicap Inventory (DHI), Neurobehavioral Symptom Inventory (NSI), Behavioral Symptom Inventory-18 (BSI-18), and Pittsburgh Sleep Quality Index (PSQI).

EXAMPLES

Example 1

To investigate the potential for using CBD and psilocybin to treat TBI and mTBI, animal studies using the CBD and psilocybin were conducted. It was found that concomitant administration of 5 mg of CBD [5 mg/kg] and 1.5 mg of psilocybin [1.5 mg/kg]) surprisingly demonstrated advantages over the administration of each compound alone, and over controls, in a variety of tests.

In a fluid percussion model the CBD/psilocybin combination (5 mg/kg CBD and 1.5 mg/kg psilocybin was given PO beginning one hour after an injury and continued daily for 7 total doses) outperformed each component and vehicle when working memory was tested at 21 days after injury, as indicated by lower latency time on trial 2, the results of which are shown in FIG. 1. In this task, rats were placed in a water maze and challenged to find the quadrant with the platform. The time required to find the platform is measured. Since the platform is not moved, rates should show a shorter time to find the platform on the second trial (done at a specified time after the first trial). Shorter time indicates better working memory. As can be seen in FIG. 1, the combination of CBD and psilocybin resulted in the fastest latency period for the second trial.

Figure 2:
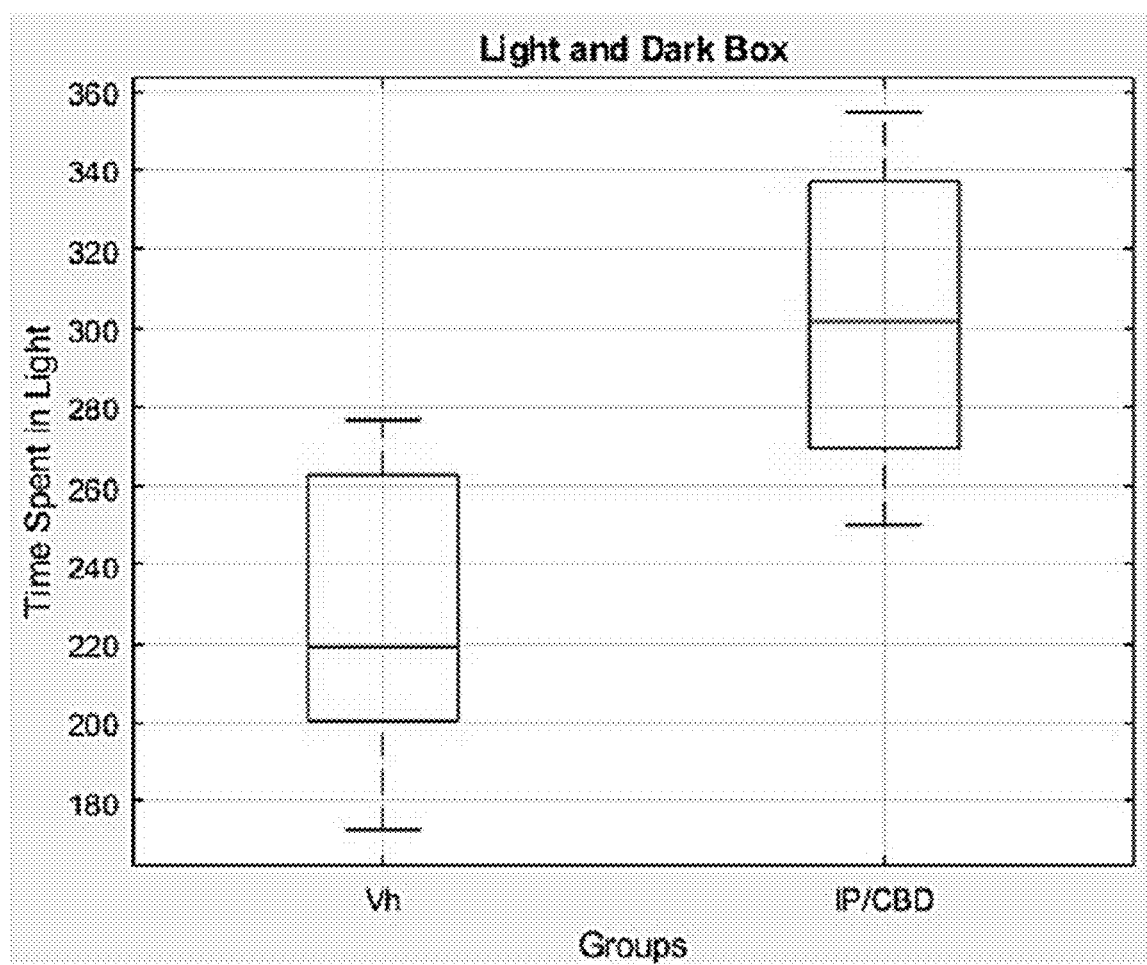
FIG. 2 is a graphical illustration of a Rat Blast Model.

It was also shown in this same model that the combination of psilocybin and CBD leads to a dramatic reduction in contusion volume. In a rat blast model of TBI, animals were intraperitoneal (IP) dosed with CBD and PO dosed with psilocybin (5 mg/kg of CBD and 1.5 mg/kg psilocybin beginning one hour after the injury for 7 total doses) demonstrated significantly less stress than vehicle alone (sterile water via gavage) as indicated by more time spent in light in the light dark box, as shown in FIG. 2. This increased time spent in light was not seen with either CBD or psilocybin when dosed separately.

Example 2

Another study was conducted in rats to evaluate the synergy of an oral combination of psilocybin and CBD in mitigating TBI-induced pathology in a preclinical model of TBI. In this study, adult rats were exposed to a moderate fluid-percussion pulse over the right parietal cortex.

Figure 3:
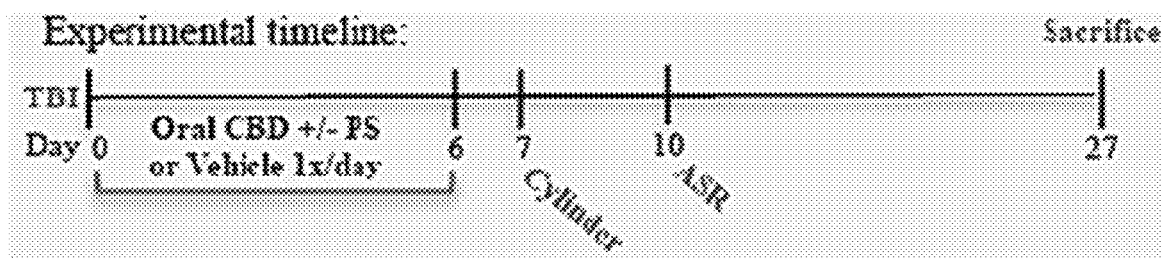
FIG. 3 is a timeline of injury, dosage administration and testing.

Psilocybin (1.5 mg/kg) and/or CBD (5 mg/kg) in 1 mL of ddH2O (or vehicle/ddH2O alone) was dosed by oral gavage at 1-hour post-injury, and for 1×/day for 6 consecutive days thereafter, resulting in 7 total dosage administrations. Animals receiving psilocybin+CBD were exposed to a traumatic/fearful stimulus (predatory urine) to evaluate anxiety-like behavior. Outcome measurements included sensorimotor (cylinder test), cytoprotection (volumetric analyses of contusion and cortical atrophy), and neuroinflammation (microglia reactivity). The timeline of the injury, as well as the dosage administrations and tests is shown in FIG. 3.

Figure 4:
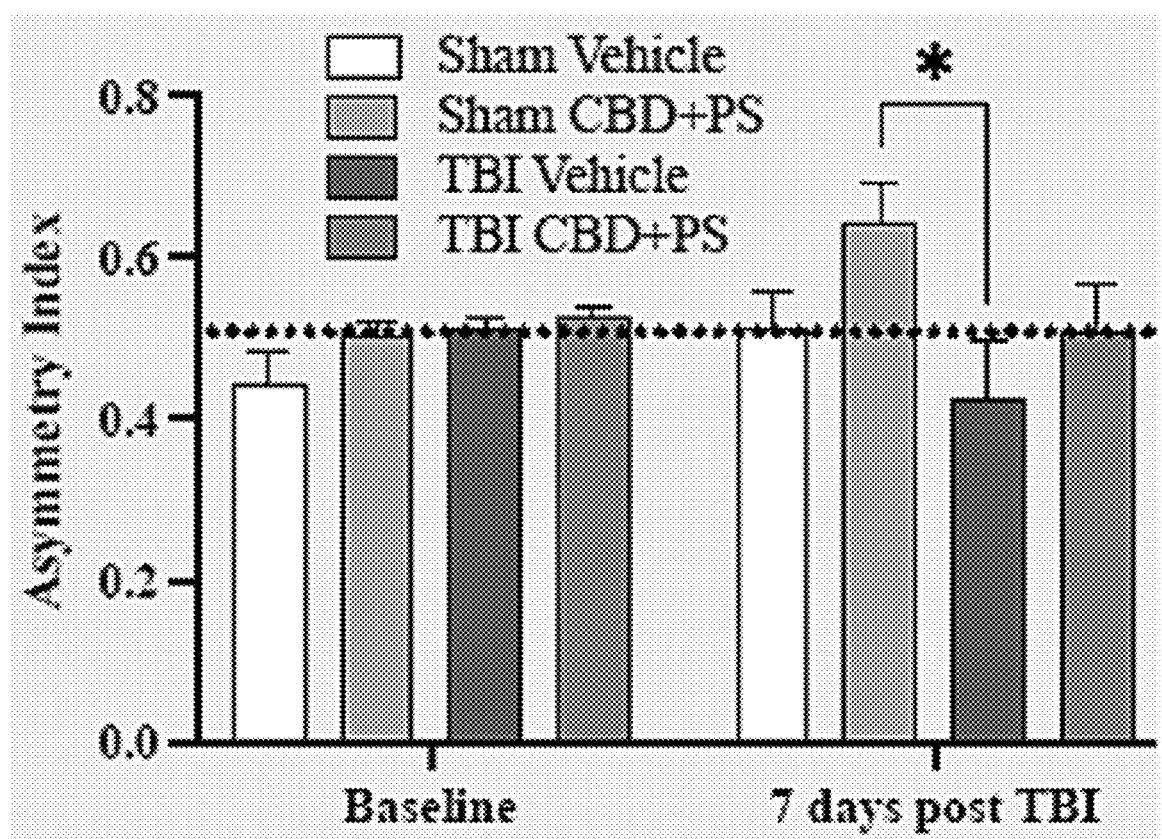
FIG. 4 is a graphical illustration of symmetry index of forelimb placements based on varying dosage administrations.

As can be seen in FIG. 4, results showed that symmetry index of forelimb placements assessing sensorimotor capacity after CBD+psilocybin treatment reversed injury-induced deficits 7 days post TBI, as compared to vehicle.

Figure 5:
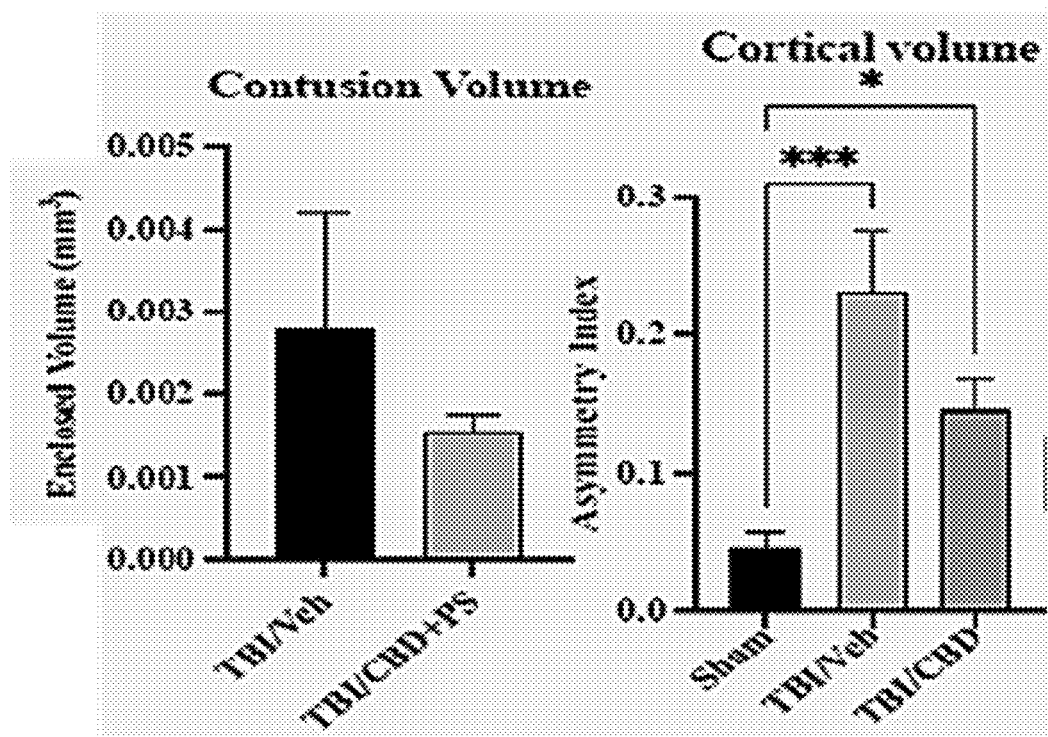
FIG. 5 is a graphical illustration of Contusion Volume and Cortical Volume for various samples.

Approximately 4 weeks after injury, the rats were sacrificed for histological assessment where nonbiased stereological volumetric analyses revealed, as illustrated in FIG. 5, that TBI/CBD+psilocybin animals exhibited reduced cortical contusions (left panel) and TBI/CBD-alone animals trended positively towards normalization of cortical volume atrophy (right panel) relative to injured vehicle-control animals.

Figure 6:
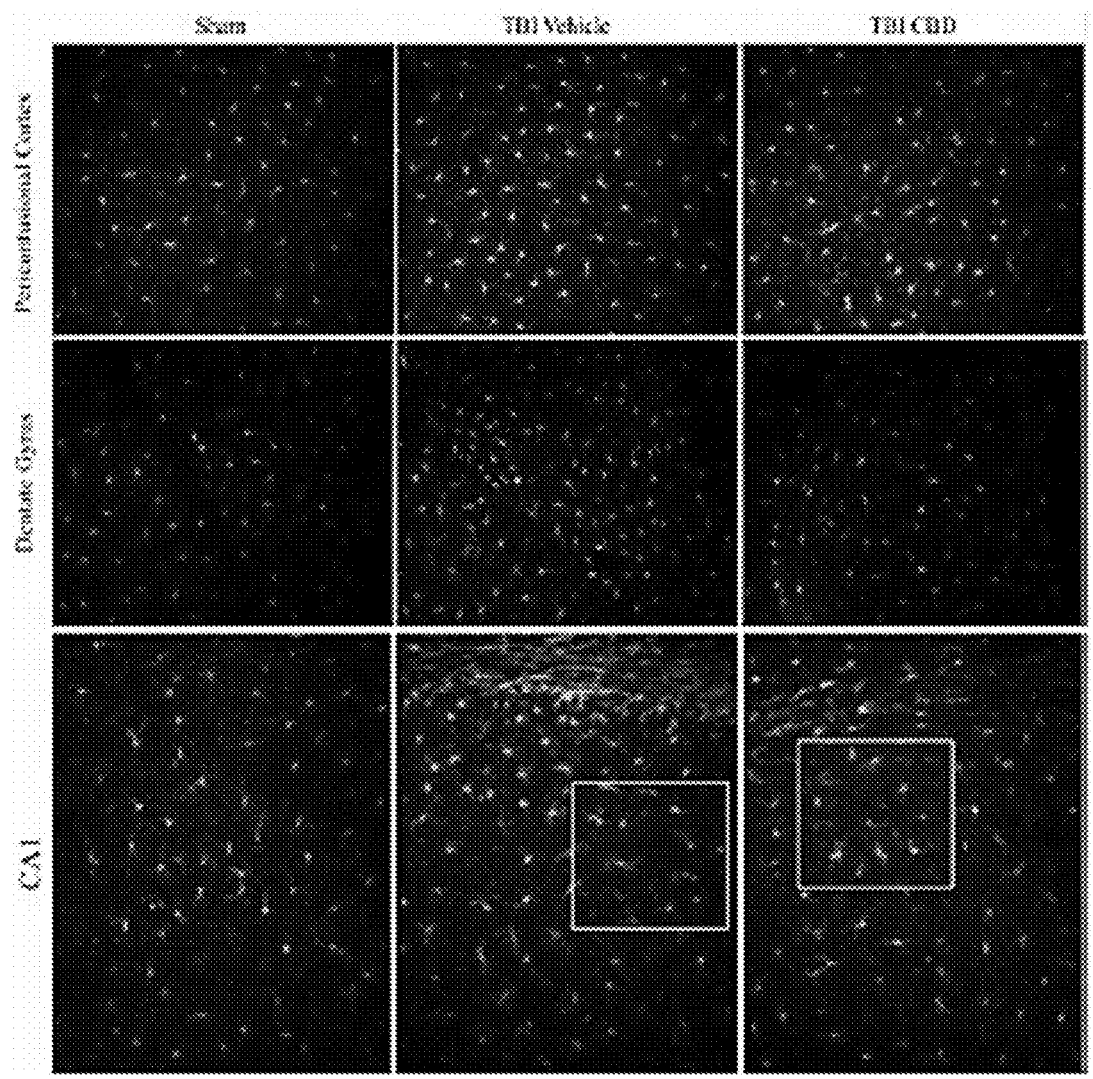
FIG. 6 are images of immunohistochemical analysis results of various samples.

Immunohistochemical data in rats is shown in FIG. 6. Immunohistochemical analyses demonstrated normalization of injury-induced Iba+microglia changes with CBD-alone administration at a CBD dosage (5 mg/kg). In pericontusional cortex (top row) there was a reduced density of Iba1+ cells. In the ipsilateral hippocampus, Iba1+ cells in dentate gyrus (middle row) appeared significantly greater in number in controls compared to CBD group. In CA1 (bottom row), while no overt differences were observed in cell density, reactive morphological alterations were more pronounced in the injured-vehicle group. Boxes demarcate representative cells in which changes could be compared. TBI/Vehicle had cells with shorter thicker processes and compact cell bodies, while CBD-treatment seemed to reduce reactive microglia morphology, resembling sham animals to a greater degree.

Figure 7:
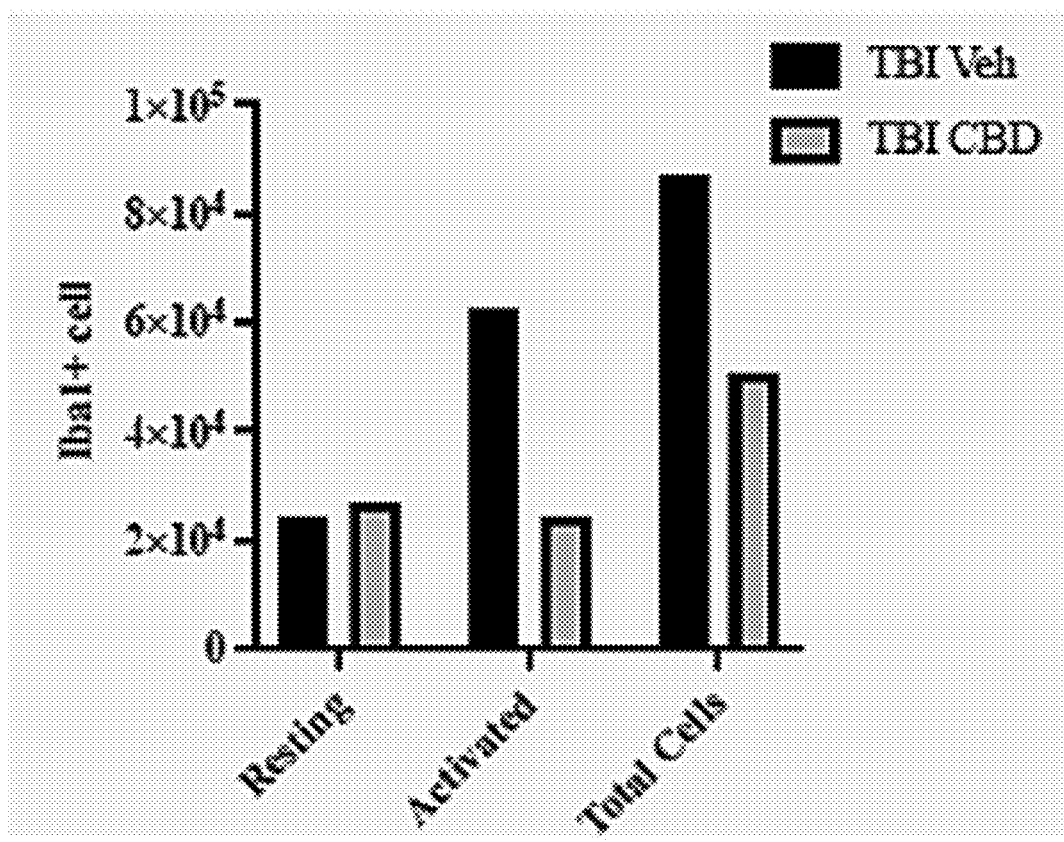
FIG. 7 is a graphical illustration of Iba1+ Phenotype in Cortical Contusion results from various samples.

As shown in FIG. 7, in the cortical penumbra, preliminary quantitative analyses showed CBD administration significantly decreased activated microglia phenotypes in rats and reduced overall microglia numbers, two hallmark indicators of TBI-induced neuroinflammation.

Results of this study, Example 2, where rats were exposed to a moderate fluid-percussion pulse over the right parietal cortex, CBD alone, and in combination with psilocybin has been shown to mediate neuroprotection and inflammatory pathways. Analyses showed reduction in microglial reactivity and overall numbers as well as positive effects in behavioral and histopathological outcomes.

It was observed that sham/CBD+psilocybin groups had significantly increased startle reflexes relative to all other groups. This is speculated to be due to increased awareness and heightened sensitivity of surroundings as compared to control groups. The therapeutic potential of CBD and psilocybin after brain injury includes neuroprotection, anti-apoptosis, and anti-inflammation. Based on this data, it is believed that clinically relevant administration of CBD alone or in combination with psilocybin would mitigate some of the behavioral deficits, cytoarchitecture disruption, and reduce neuroinflammatory responses after moderate TBI.

The results of the animal studies showed positive effects of CBD delivered interperitoneally in a rat model of mTBI. In vitro and in vivo studies suggest that psilocybin may influence the treatment of mTBI in both the acute and chronic phases by modulating neuroinflammation, neuroplasticity, hippocampal neurogenesis, and increase in brain complexity.

The above pre-clinical studies demonstrate that co-administration of CBD and Psilocybin could act synergistically to control the symptoms of TBI and mTBI in patients. Also, administration of CBD and Psilocybin could aid to control comorbidities including stress and anxiety which can delay recovery from the injury. It is believed that the mechanism of action of CBD for this indication involves its known $CB_2$ receptor agonist activity and resultant neuroprotectant effects, reducing inflammation and gliosis. It is believed that Psilocybin's mechanism of action to reduce the comorbidities associated with mTBI involves, at least in part, its activity as an agonist of 5HT2A serotonin receptors.

The strategy to co-administer CBD and Psilocybin in patients is based on animal studies and clinical observations that mTBI can be associated with stress, anxiety, and other comorbidities that interfere with the healing process. Also, the addition of psilocybin to the CBD dosage alleviates the co-morbidities that interfere with healing, thus promoting the activity of CBD on the primary injury.

Example 3

In this example, rats were exposed to two moderate fluid-percussion pulses over the right parietal cortex, and were also exposed to a traumatic/fearful stimulus (predatory urine). The rats were given three different dosage combinations by gavage, once per day, for seven days. The three dosages are shown in the results of FIGS. 8A-8D, and are as follows: CBD 5 mg/Psilocybin 0.03 mg (yellow bar); CBD 15 mg/Psilocybin 0.10 mg (blue bar); and CBD 25 mg/Psilocybin 0.17 mg (gray bar). The control, or "vehicle" data are shown in the orange bars of FIGS. 8A-8D.

Figure 8A:
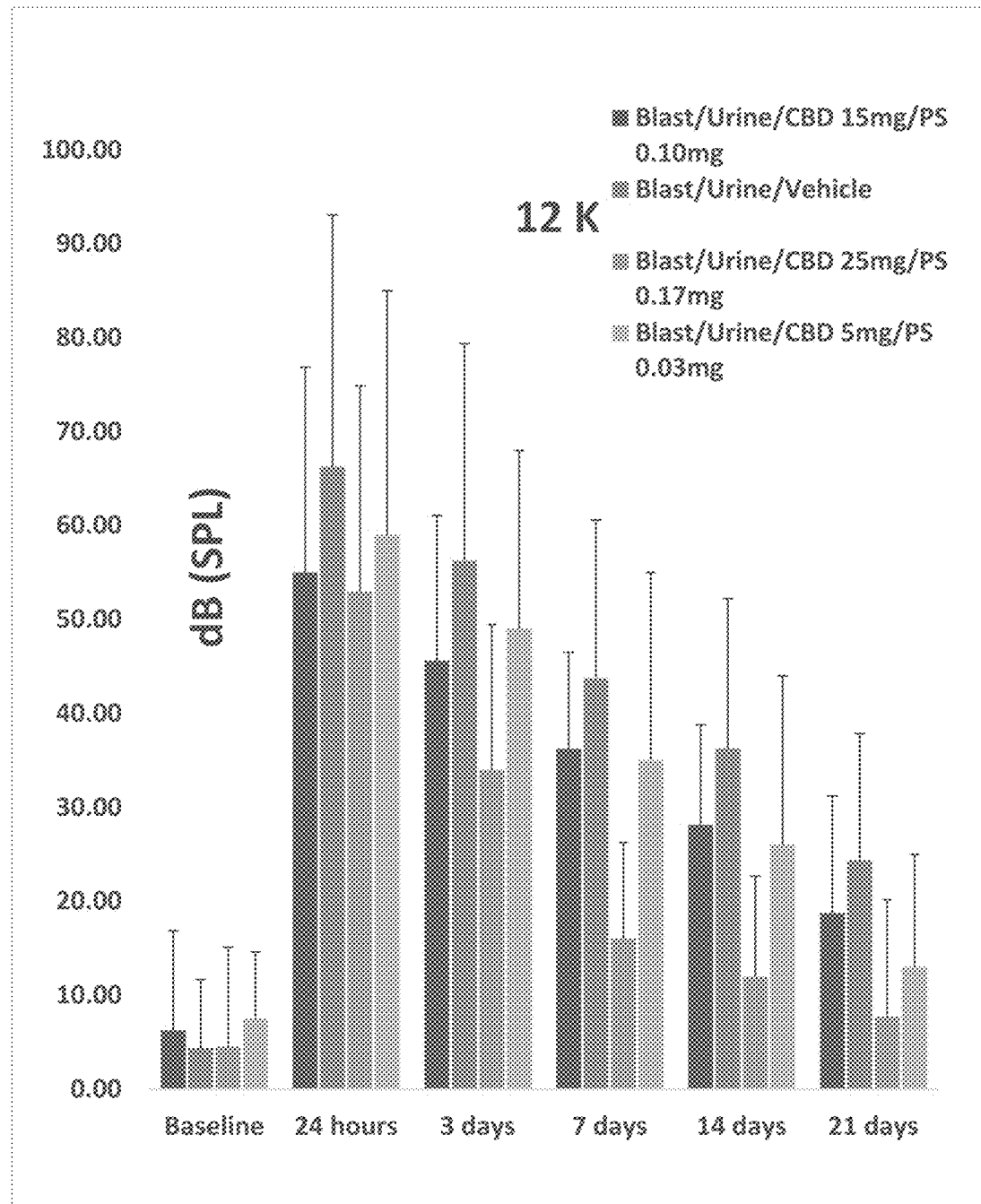
FIGS. 8A-8D are graphical illustrations of hearing tests results at varying frequencies.
Figure 8B:
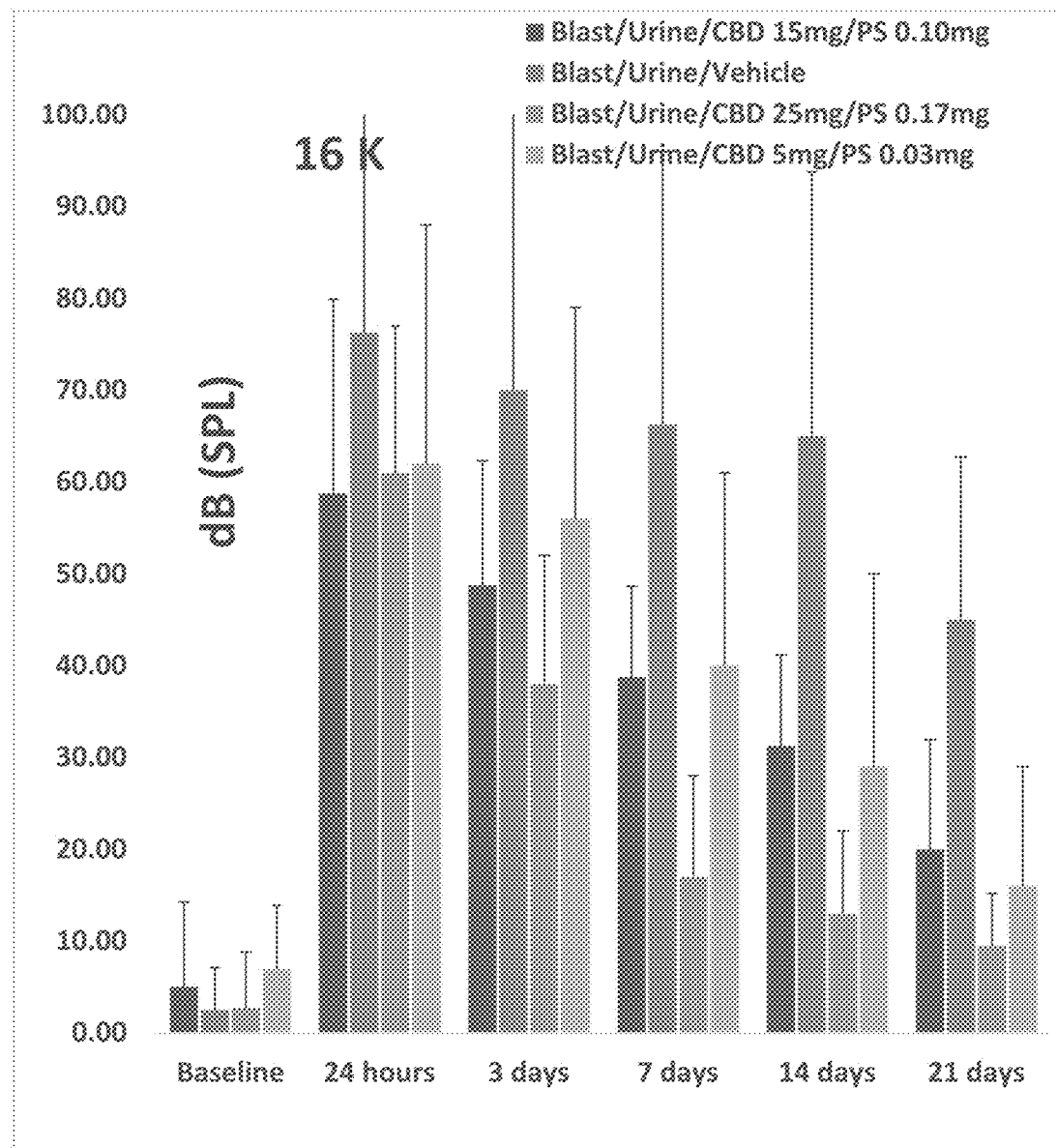
Figure 8C:
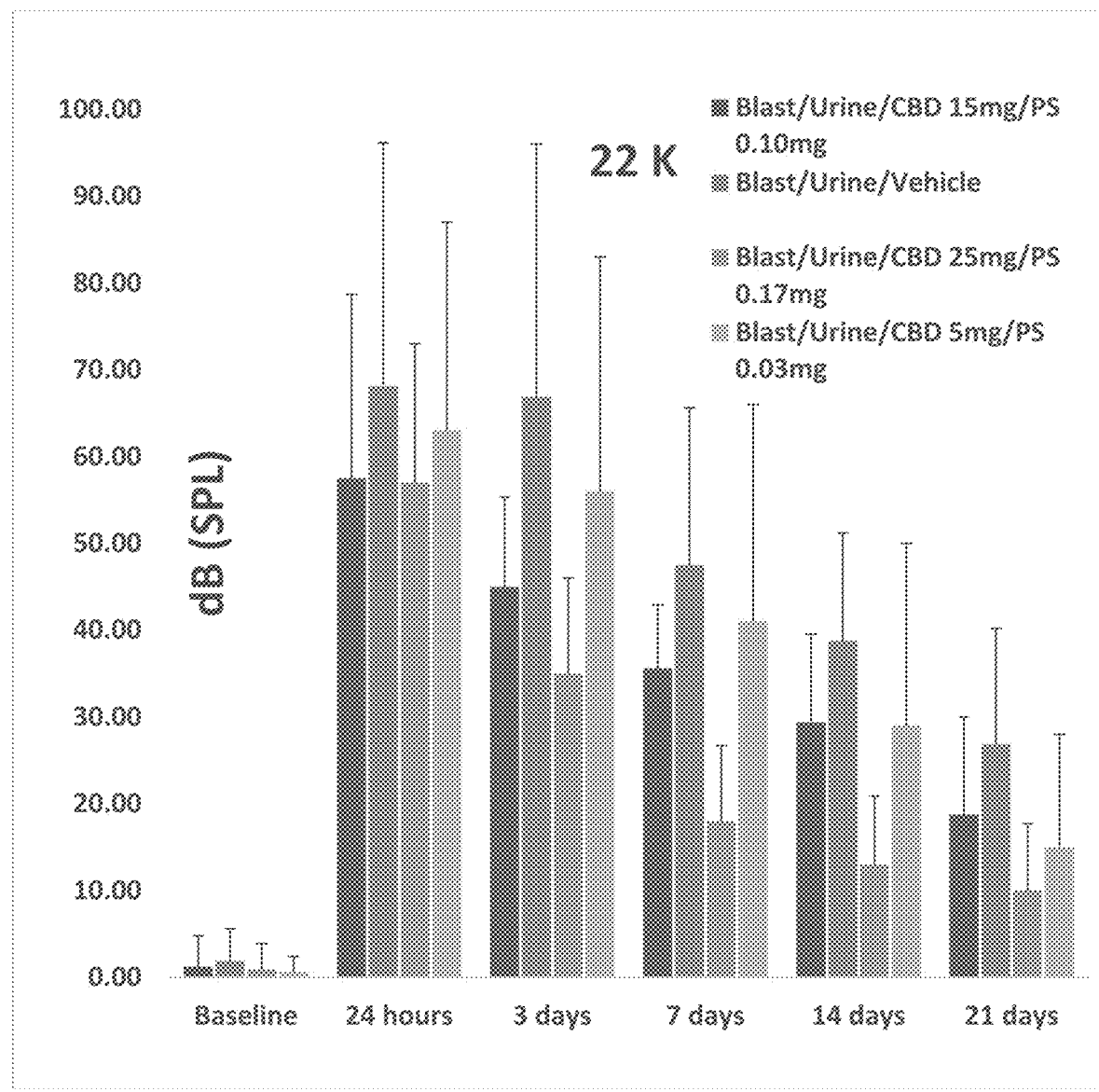
Figure 8D:
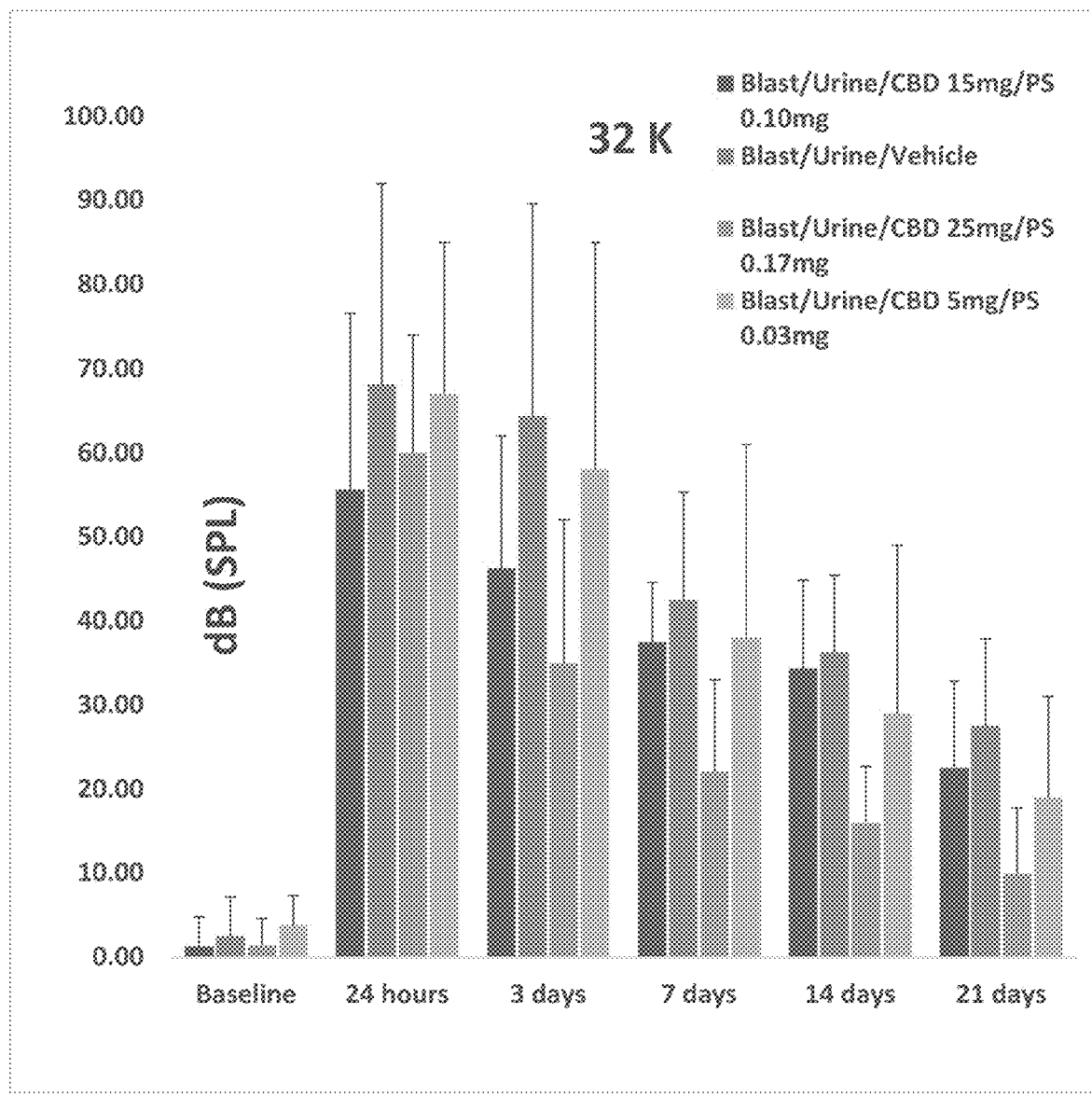

At days 1, 3, 7, 14, and 21 post injury, the rats were given hearing tests at the following frequencies 12,000 Hz, 16,000 Hz, 22,000 Hz, and 32,000 Hz. The results are illustrated for each frequency in FIGS. 8A-8D, specifically FIG. 8A illustrating results at 12,000 Hz, FIG. 8B illustrating results at 16,000 Hz, FIG. 8C illustrating results at 22,000 Hz, and FIG. 8D illustrating results at 32,000 Hz.

As can be seen in FIGS. 8A-8D, the treated groups of rats performed significantly better than vehicle at all frequencies, and at all time points post injury. The highest dose, CBD 25 mg/Psilocybin 0.17 mg (gray bar) was highly significantly more effective at reducing hearing loss as compared to the vehicle at all time points post injury and across all frequencies.

The described embodiments and examples of the present disclosure are intended to be illustrative rather than restrictive, and are not intended to represent every embodiment or example of the present disclosure. While the fundamental novel features of the disclosure as applied to various specific embodiments thereof have been shown, described and pointed out, it will also be understood that various omissions, substitutions and changes in the form and details of the devices illustrated and in their operation, may be made by those skilled in the art without departing from the spirit of the disclosure. For example, it is expressly intended that all combinations of those elements and/or method steps which perform substantially the same function in substantially the same way to achieve the same results are within the scope of the disclosure. Moreover, it should be recognized that structures and/or elements and/or method steps shown and/or described in connection with any disclosed form or embodiment of the disclosure may be incorporated in any other disclosed or described or suggested form or embodiment as a general matter of design choice. Further, various modifications and variations can be made without departing from the spirit or scope of the disclosure as set forth in the following claims both literally and in equivalents recognized in law.

What is claimed is:

1. A method for treating brain injuries comprising:
    administering to a patient a first oral dosage form comprising about 100 mg to about 300 mg of cannabidiol (CBD); and
    administering to the patient, concomitantly with the first oral dosage form, a second oral dosage form comprising about 1 mg to about 5 mg of Psilocybin, wherein a ratio between the first oral dosage form and the second oral dosage form is about 145:1 to about 155:1, wherein the treatment is for TBI.

2. The method of claim 1, wherein the treatment is for mTBI.

3. The method of claim 1, wherein the first oral dosage form comprises about 250 mg to about 300 mg CBD and the second oral dosage form comprises about 1.25 mg to about 2.5 mg Psilocybin.

4. The method of claim 1, wherein the administration of the first oral dosage form and the second oral dosage form occurs twice a day, for about seven days to about 10 days.

5. The method of claim 1, wherein the administration of the first oral dosage form and the second oral dosage form occurs once a day, for about seven days to about 10 days.

6. The method of claim 1, wherein a first administration of the first oral dosage form and the second oral dosage form occurs within about 72 hours of the time of the brain injury.

7. The method of claim 1, wherein a first administration of the first oral dosage form and the second oral dosage form occurs within about 1 hour of the time of the brain injury.

8. A method of activating both a CB2 receptor and a 5HT receptor of a patient, the method comprising:
    administering to the patient a first oral dosage form comprising about 100 mg to about 300 mg of cannabidiol (CBD); and
    administering to the patient, concomitantly with the first oral dosage form, a second oral dosage form comprising about 1 mg to about 5 mg of Psilocybin, wherein a ratio between the first oral dosage form and the second oral dosage form is about 145:1 to about 155:1, and wherein the patient has a TBI.

9. The method of claim 8, wherein the administration of the first oral dosage form and the second oral dosage form occurs twice a day, for about seven days to about 10 days.

10. The method of claim 8, wherein the administration of the first oral dosage form and the second oral dosage form occurs once a day, for about seven days to about 10 days.

11. A method of reducing a contusion volume of a mammal, the method comprising:
    administering to the mammal a first oral dosage form comprising about 100 mg to about 300 mg of cannabidiol (CBD); and
    administering to the mammal, concomitantly with the first oral dosage form, a second oral dosage form comprising about 1 mg to about 5 mg of Psilocybin, wherein a ratio between the first oral dosage form and the second oral dosage form is about 145:1 to about 155:1, and wherein the patient has a TBI.

12. The method of claim 11, wherein the administration of the first oral dosage form and the second oral dosage form occurs twice a day, for about seven days to about 10 days.

13. The method of claim 11, wherein the administration of the first oral dosage form and the second oral dosage form occurs once a day, for about seven days to about 10 days.

14. The method of claim 11, wherein a first administration of the first oral dosage form and the second oral dosage form occurs within about 72 hours of the time of the contusion.

15. The method of claim 11, wherein a first administration of the first oral dosage form and the second oral dosage form occurs within about 1 hour of the time of the contusion.

16. The method of claim 1, wherein the administration of the first oral dosage form and the second oral dosage form occurs each day, for about seven days to about 10 days.

17. The method of claim 1, wherein the first oral dosage form is a different dosage form than the second oral dosage form.

18. The method of claim 8, wherein the first oral dosage form is a different dosage form than the second oral dosage form.

19. The method of claim 11, wherein the first oral dosage form is a different dosage form than the second oral dosage form.

* * * * *